United States Patent [19]

Lagowski

[11] Patent Number: 5,369,495

[45] Date of Patent: Nov. 29, 1994

[54] SEMICONDUCTOR CONTAMINANT SENSING SYSTEM AND METHOD

[75] Inventor: Jacek Lagowski, Tampa, Fla.

[73] Assignee: University of South Florida, Tampa, Fla.

[21] Appl. No.: 940,527

[22] Filed: Sep. 4, 1992

[51] Int. Cl.5 ...................... G01N 21/25; G01N 21/89
[52] U.S. Cl. .................................. 356/418; 324/71.5; 356/237
[58] Field of Search ............... 356/418, 237; 324/71.5; 73/61.69, 61.41, 61.62

[56] References Cited

U.S. PATENT DOCUMENTS

| 4,333,051 | 6/1982 | Goodman | 324/158 R |
| 4,433,288 | 2/1984 | Moore | 324/158D |
| 4,454,472 | 6/1984 | Moore | 324/158 R |
| 4,598,249 | 7/1986 | Goodman et al. | 324/158 R |
| 4,758,786 | 7/1988 | Hafeman | 324/158 D |
| 4,836,012 | 6/1989 | Doty et al. | 324/71.5 X |
| 4,891,584 | 1/1990 | Kamieniecki et al. | 324/158 R |
| 5,025,145 | 6/1991 | Lagowski | 250/211 J |
| 5,087,876 | 2/1992 | Reiss et al. | 324/158 D |
| 5,091,691 | 2/1992 | Kamieniecki et al. | 324/158 R |

OTHER PUBLICATIONS

Nikkei Microdevices, May 1990, p. 54.
"Monitoring of Heavy Metal Contamination During Chemical Cleaning with Surface Photovoltage," L. Jastrzebski, et al, presented at Second International Symposium on Cleaning Technology in Semiconductor Device Manufacturing, Phoenix, Ariz., Oct., 1991.
"Non-Contact Mapping of Heavy Metal Contamination for Silicon IC Fabrication," J. Lagowski, P. Edelman, M. Dexter and W. Henley, Semiconductor Science and Technology, 1991, in press.
"A Method for the Measurement of Short Minority Carrier Diffusion Lengths in Semiconductors", Alvin M. Goodman, Journal of Applied Physics, vol. 32, No. 12, Dec. 1961.
"Theory of the Small-Signal Photovoltage at Semiconductor Surfaces," D. R. Frankl and E. A. Ulmer, Dept. of Physics, The Pennsylvania State University, University Park, Pa., Jun. 1966.

Primary Examiner—Vincent P. McGraw
Assistant Examiner—K. P. Hantis
Attorney, Agent, or Firm—Calfee, Halter & Griswold

[57] ABSTRACT

Contamination of a fluid medium is measured using a thin-wafer sensor having a front surface and a back surface. The thin-wafer sensor is made of relatively pure p-type silicon and has a thickness less than the bulk diffusion length of the material. The back surface is placed in physical contact with the fluid being monitored either by building the sensor into a fluid testing chamber in line with the system using the fluid, or by immersing an encapsulated version of the sensor into the fluid medium. A photovoltaic generating and sensing system generates and measures e.g., the surface photovoltage (SPV), at the front surface. A series of SPVs are measured and used to derive the minority carrier diffusion length L of the sensor. The carrier diffusion length value is used to calculate the surface recombination velocity at the back surface. The surface recombination velocity value is used to determine the surface concentration of contaminants at the back surface, which may be used to calculate the concentration of contaminants in the fluid medium.

33 Claims, 7 Drawing Sheets

SEMICONDUCTOR CONTAMINANT SENSING SYSTEM AND METHOD

TECHNICAL FIELD

The present invention relates to a new and useful system and method for sensing contamination of a fluid medium, particularly metal contamination of a fluid medium used in the production of integrated circuitry in semiconductor wafers.

BACKGROUND OF THE INVENTION

The production of integrated circuits ("ICs") in semiconductor materials generally involves bringing different fluids into direct contact with the semiconductor materials. For example, in the production of ICs in silicon (Si) and/or gallium arsenide (GaAs) wafers, it is common to bring gases or liquid chemicals into contact with the wafers for purposes such as: (i) cleaning, (ii) etching, (iii) application of resists, etc.

It is well known that metal impurities present in the gases or liquid chemicals used in processing semiconductor materials have a profound detrimental effect on manufacturing yield and the performance of integrated circuits. These impurities, present in starting gases or liquid chemicals, or generated by equipment failures, react with the semiconductor materials to form electron hole recombination centers which degrade the semiconductor materials and any integrated circuits produced therefrom.

In processing semiconductor materials, metal impurities are difficult to monitor and control, due to the very low threshold concentrations required for IC yield degradation. The range of surface contamination of most interest in the semiconductor industry is between $10^8$ atoms/cm$^2$ and $10^{12}$ atoms/cm$^2$. The problem is even more complex due to the wide variability of the contaminating power of different chemicals used in IC processing. For example, $NH_3OH$ with 0.1 ppm of iron (Fe) will leave about $10^{12}$ Fe atoms/cm$^2$ on a silicon surface, which is extremely damaging, while hydrogen fluoride (HF) with the same Fe concentration will cause only marginal contamination on the level of $10^9$ Fe atoms/cm$^2$.

Thus, as a quality control measure during the production of ICs, it is common to measure the contamination of the fluid medium(s) which contact the semiconductor materials for metal impurities which degrade the quality of the semiconductor material(s). For example, it is common to measure the contaminants in the fluid medium(s) before and after processing to ensure that undue contamination has not occurred. One method of measuring the extent of the contamination of the fluids is by spectroscopy. However, this method of testing is not suitable for continuous monitoring the fluid because a sample of the fluid must be removed periodically from the system for testing. Meanwhile, the wafers processed by the contaminated fluids before the contamination is detected become contaminated themselves. These contaminated wafers may undergo at least partial processing into chips—processing that is wasteful because the wafer is already contaminated.

One common method for determining the contamination of the processed wafers measures a property of the semiconductor known as the minority carrier diffusion length "L". The minority carrier diffusion length indicates the effective distance that excess carriers diffuse through a semiconductor during their lifetime. Excess carriers in a semiconductor tend to redistribute due to a diffusion phenomenon which equalizes the carrier concentration. The fewer the recombination sites, the farther the excess carriers can diffuse before they recombine. In other words, longer measured diffusion lengths correspond to fewer recombination sites. This diffusion process is controlled by the mobility of the excess minority carriers "$\mu$" and their lifetime "$\tau$". The diffusion length L is a parameter combining these two factors, and in the simplest case has the form:

$$L = \left( \frac{kT}{q} \mu \tau \right)^{\frac{1}{2}}$$

where k is Boltzman's constant, T is the temperature in Kelvin, and q is the elementary charge.

As discussed above, metal contaminants in silicon wafers act as recombination centers which reduce the minority carrier lifetime $\tau$. By measuring the diffusion length L, the concentration of the contaminants may then be determined by using the relationship $N_c \approx C\tau^{-1}$ (where $N_c$ is the concentration of heavy metal contaminants, and C is a constant depending on the individual impurity).

A common, nondestructive technique for measuring the diffusion length L takes advantage of the process by which light impinging upon a semiconductor surface may be absorbed and produce excess carriers (holes and electrons) if the energy of the incident photons, "hv", is above the semiconductor energy band gap "$E_g$". As a result of this photogeneration and diffusion process, a certain number of electron-hole pairs reach the proximity of the surface and become separated by the electric field of the surface-space charge region to produce a photovoltaic effect refered to as "surface photovoltage" (SPV). Measurement of the surface photovoltage can thus be used for the determination of the minority carrier diffusion length L, in turn for the determination of the lifetime $\tau$, and hence for a determination of the concentration of the heavy metal contaminants $N_c$.

Some prior techniques for determining the diffusion length from the surface photovoltage rely on a procedure known as the "Constant Magnitude Surface Photovoltage" (CMSPV) technique, the principles of which were proposed by Goodman in "A Method for the Measurement of Short Minority Carrier Diffusion Lengths in Semiconductors," J. Appl. Phys. Vol. 33, p. 2,750, 1961; subsequently adopted as the ASTM standard ANSI/ASTM F-391-78 p. 770, 1976 and discussed in U.S. Pat. No. 4,337,051.

The characteristic steps of the foregoing techniques are to measure the photovoltage and the photon flux at several wavelengths ($\lambda_1 \ldots \lambda_i$) (corresponding to photon energies (hv$_1 \ldots$ hv$_i$)); vary the magnitude of the photovoltage by adjustment of the incident light intensity or photon flux ($\phi$) to produce a constant photovoltage; measure the corresponding photon fluxes ($\phi_1 \ldots \phi_i$); and then plot the photon flux values versus the reciprocal absorption coefficient $\alpha^{-1}$ of the semiconductor sample at the various photon energies. This plot is then linearly extrapolated to determine the intercept along the reciprocal absorption coefficient axis to obtain the minority carrier diffusion length L (i.e., $L = -\alpha^{-1}$ where I=O). Thus, in the CMSPV techniques, the diffusion length is determined from the corresponding values of the photon fluxes ($\phi_1 \ldots \phi_i$)

required to maintain the constant magnitude SPV signal $V_1=V_2=V_3\ldots$.

A more recent technique for determining the diffusion length L is disclosed in the applicant's U.S. Pat. No. 5,025,145. According to this technique, an induced photovoltage is first measured for different photon fluxes to assure linearity of photovoltage versus photon-flux. Next, using light with constant photon flux of the value within the linear photovoltage range, the photovoltage is measured for a series of selected photon energies and those photovoltage values which monotonically increase with the photon energy are plotted as a function of the reciprocal absorption coefficient corresponding to the given photon energies. The minority carrier diffusion length is determined by extrapolation to find the reciprocal absorption coefficient at zero photovoltage (i.e., $L=-\alpha^{-1}$ where $\phi/\Delta V=0$). The values outside of the monotonical range are rejected from the analysis, which eliminates interference from the surface effects and assures an accurate determination of the diffusion length. This method determines diffusion length directly from the surface photovoltage measured in the different incident photon energies.

Additional background information on sensing metal contamination of semiconductor wafers may be found in J. Lagowski, et al., "Non-Contact Mapping of Heavy Metal Contamination for Silicon IC Fabrication", Vol. 7, *Semiconductor Science & Technology*, A185-A192 (1992), a copy of which is attached hereto as Exhibit A and is made part of this disclosure.

Several methods exist to take SPV measurements. One method is the contact electrode, wherein a semi-transparent material such as indium tin oxide (ITO) is placed in contact with the silicon surface being illuminated. Another method is to capacitively couple the SPV to an electrode. One specific type of capacitive coupling electrode is the non-contact electrode. With a non-contact electrode, the dielectric is air, which allows the wafer being tested to remain untouched by the electrode. The Lagowski, et al. paper, Exhibit A, has a specific discussion of capacitive coupling and non-contact sensing of SPVs at pages A187–88.

In both of the SPV techniques discussed above, a semiconductor wafer is used as a sensor, and the surface photovoltage is measured at the surface that was in direct contact with the fluid medium. In the applicant's experience, the wafer used in such techniques would have a thickness which is considerably greater than its bulk diffusion length—typically, at least twice as thick.

However, in these thick-wafer SPV methods, the configuration is such that the measured parameter, i.e., the minority carrier diffusion length, is sensitive to the recombination centers in the bulk, but is not sensitive to surface contaminants. Therefore, to test for contamination, the contaminants, which typically form on the surface of the wafer, are annealed into the wafer at a high temperature in an additional processing step. For example, a test wafer is included with the wafers that were being processed. After a various number of processing steps are complete, the process is shut down and the test wafer is annealed and analyzed to determine the amount of contamination the batch has sustained. Therefore, these methods of determining the extent of contamination are believed not suitable for constant monitoring of fluids used in semiconductor processing.

SUMMARY OF THE PRESENT INVENTION

The present invention provides a semiconductor contamination monitoring system and method in which a relatively thin wafer is used as a sensor, and photovoltaic measurements (such as SPV measurements) are taken at the surface of the wafer which is opposite from the surface in contact with the fluid medium to determine if the wafer evidences an undesirable level of contamination in the fluid medium. Thus, the sensor can be employed in a "continuous" type semiconductor processing system, with the sensor located in a sensing chamber disposed upstream of a semiconductor processing chamber.

Specifically, according to the invention, a sensor is preferably formed in the shape of a wafer having a front surface and a back surface. The back surface of the wafer has a very low surface recombination value and is in direct contact with the fluid medium, while the front surface of the wafer has a depletion-type surface barrier. The sensor is preferably made from relatively pure silicon or other semiconductor material which is reactive with semiconductor contaminants to form recombination centers at the back surface and which enables generation and diffusion of electrons and holes therethrough. Further, the wafer has a bulk diffusion length and a thickness such that the magnitude of surface photovoltage developed at the front surface by means of light at a predetermined excitation state is dependent on the concentration of semiconductor contaminants at the back surface of the wafer. According to the preferred form of the invention, the wafer has a thickness that is less than the bulk diffusion length of the wafer.

Additionally, according to the invention, a photovoltaic generating/measuring device is provided for: (i) directing light at the predetermined excitation state at the front surface of the wafer to develop a photovoltaic effect (e.g., a surface photovoltage), and (ii) measuring the magnitude of the photovoltaic effect (e.g., the surface photovoltage) at or near the front surface. The changes in the magnitude of the photovoltaic effect can then used to determine whether the fluid sample evidences an undue level of semiconductor contaminants.

According to the preferred embodiment, the photovoltaic generating/measuring device preferably includes:

(a) a light source for producing a light signal, (b) a filter for controlling the intensity of the light signal, (c) a chopper for controlling the wave form of the light signal, (d) a filter structure for controlling the wave length of the light signal;

(e) a pick-up electrode for sensing surface photovoltage developed at the front surface of the sensor; and (f) a detection circuit for measuring the magnitude of the surface photovoltage sensed by the pick-up electrode.

One preferred type of semiconductor processing system for the invention includes a semiconductor processing chamber and a sensing chamber disposed upstream of the semiconductor processing chamber. The sensing chamber has an inlet for receiving a sample of the fluid medium and an outlet for directing the sample of the fluid medium into the semiconductor processing chamber. The sensor wafer forms at least part of the sensing chamber with the back surface of the sensor disposed in direct contact with the fluid medium in the sensing chamber. A determination of the fluid contamination on the back surface of the wafer can thus be determined by measuring the surface photovoltage on the front surface of the wafer. Thus, contamination may be measured without interrupting the system to, e.g., anneal and measure a test wafer, and therefore, the sensor can be used as part of a "continuous" type of semiconductor processing system.

It is therefore one object of this invention to provide a system and method for detecting metal contaminants on the surface of a semiconductor wafer.

It is a further object of this invention to provide a system and method for continuously testing fluids used during semiconductor wafer processing for metal contaminants.

Additional objects of the present invention will become further apparent from the following detailed description and the accompanying drawings.

DETAILED DESCRIPTION OF THE PREFERRED EMBODIMENT

Figure 1:
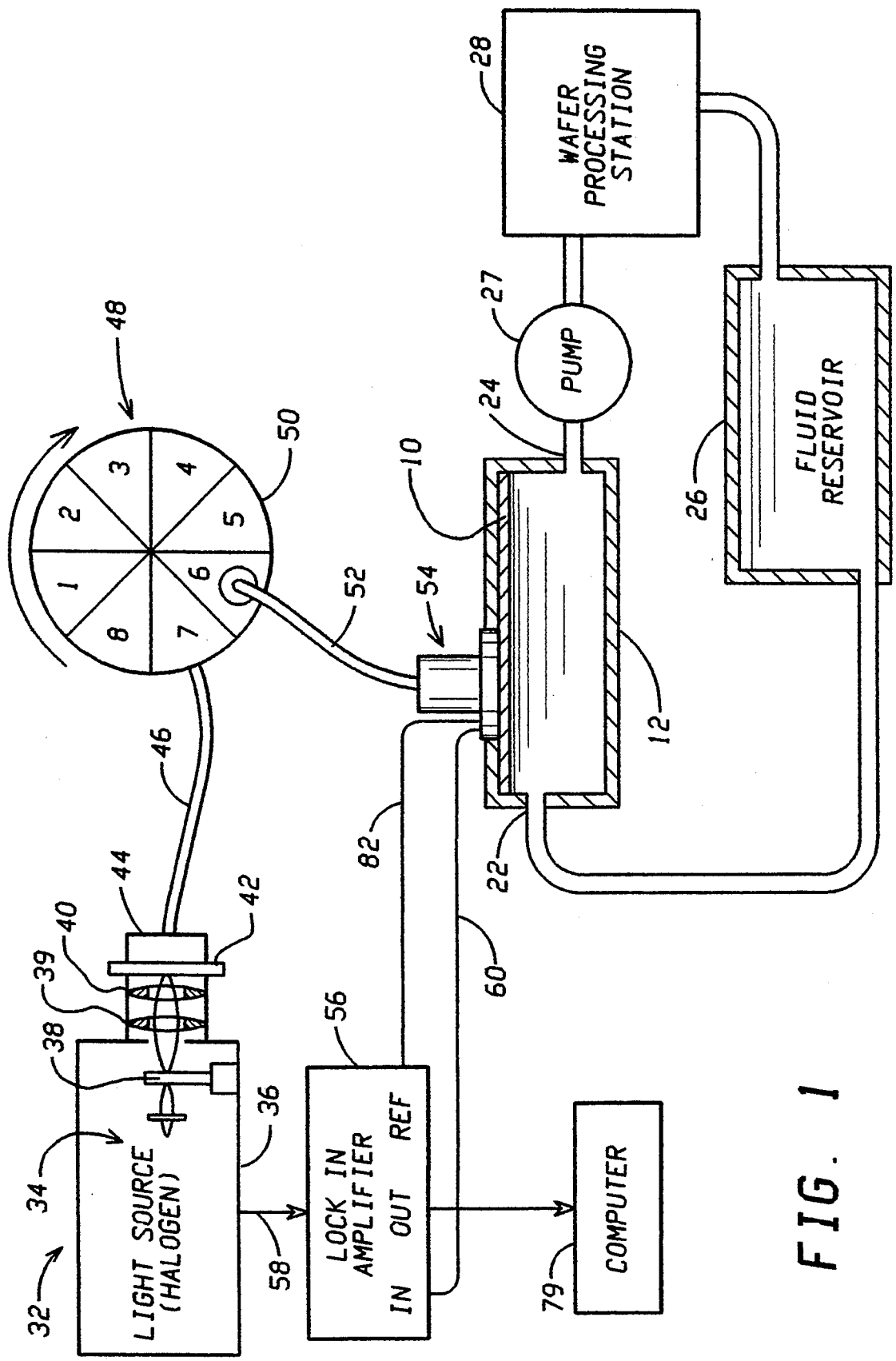
FIG. 1 is a schematic illustration of a semiconductor processing system according to the present invention.

As discussed above, a preferred application of the present invention relates to a semiconductor contamination monitoring system using an SPV silicon sensor. The sensor is preferably formed from a relatively thin, substantially pure silicon wafer, with a thickness (T) which is substantially less than its bulk diffusion length ($L^\infty$). The sensor is incorporated into a sensing chamber of the monitoring system in which a fluid medium is being tested for metal contamination. The back surface of the silicon wafer is in direct contact with the fluid medium in the chamber. The metal contaminants deposited on the back surface of the silicon sensor act as electron-hole recombination centers. Therefore, the metal contaminants change the surface photovoltage measured on the opposite (i.e., front) surface of the silicon wafer. Using SPV diffusion length measurements, the surface recombination velocity can be determined and converted into the surface concentration of deposited metals on the back surface of the silicon wafer.

Principle of the SPV Sensor

The underlying principle behind this invention is the applicant's recognition that for thin sensor wafers (i.e., with a thickness (T) less than bulk diffusion length ($L^\infty$)), the magnitude of the photovoltaic effect at the front surface of the wafer is sensitive to surface recombination at the back surface of the wafer. For example, two parameters can be measured, the minority carrier diffusion length "L" and the surface photovoltage "$\Delta V$", which can be used to determine the back surface recombination velocity "$S_b$". Other photovoltaic effects can also be used to determine $\Delta V$, for example, P-N junction photovoltage or semi-conductor metal photovoltage. Accordingly, the terms "photovoltaic" and "photovoltaic effect" as used herein is intended to encompass these and other photovoltaic effects. Measuring these parameters enables surface contamination on the back surface of the wafer to be monitored via the surface photovoltage measurements performed on the opposite (i.e., front) surface.

According to Frankl and Ulmer (D. R. Frankl and E. A. Ulmer, *Theory of the Small-Signal Photovoltage at Semiconductor Surfaces,* Surface Science, 6 (1966), p. 115), the small signal photovoltage generated under low excitation level can be expressed as:

$$\Delta V = \phi_{eff} f(V_\phi, E_f) \frac{1}{CD} \times \frac{\alpha L^2}{\alpha^2 L^2 - 1} \times$$

$$[(S_b \alpha L - D/L) \sinh(T/L) + (\alpha D - S_b) \cosh(T/L)],$$

with:

$$C = (S_f S_b L/D + D/L) \sinh(T/L) + (S_f + S_b) \cosh(T/L);$$

where:
T is the wafer thickness;
$\phi_{eff}$ is the photon flux entering the sensor (i.e., corrected for light loss due to reflectivity of front surface);
$f(V_0, E_f)$ is a known function of the initial surface potential barrier $V_o$, and the Fermi energy in the semiconductor $E_f$;
D is the minority carrier diffusivity;
$\alpha$ is the absorption coefficient;
$\alpha^{-1}$ is the light penetration depth;
$\alpha T \gg 1$, i.e., the entire light is absorbed by the wafer;
L is the minority carrier diffusion length $L = (D\tau)^{\frac{1}{2}}$ where $\gamma$ is the minority carrier lifetime;
(we denote this value also as $L^\infty$ because it is the value measured by the SPV method when the wafer thickness increases); and
$S_f$ and $S_b$ are the surface recombination velocities on the front surface and back surface, respectively.

When used in the thick-wafer SPV method as described previously, $\Delta V$ is measured for a series of $\alpha$ values and analyzed in a way enabling a determination of L. The measuring conditions are such that the wafer thickness T is at least twice as long as the diffusion length L.

When this is the case, $\sinh(T/L) \simeq \cosh(T/L) \simeq e^{T/L}/2$ and Equation (1) reduces to a simple form:

$$\Delta V = \frac{\phi_{eff} f(V_0, E_f)}{(S_f + D/L)} \frac{\alpha L}{1 + \alpha L} \tag{2}$$

Note that in the thick-wafer case, the magnitude of the surface photovoltage $\Delta V$ depends on the surface recombination velocity $S_f$ on the front surface, but is independent of the surface recombination velocity of $S_b$ on the back surface. Equation (2) can be rewritten as:

$$\frac{\phi_{eff}}{\Delta V} = \text{const} \times (1 + \alpha^{-1} L^{-1}) \tag{3}$$

which is a basis for a standard SPV plot of:

$$\frac{\phi_{eff}}{\Delta V} \text{ vs. } \alpha^{-1}$$

yielding the L value from the $\alpha^{-1}$ at the intercept $\phi/\Delta V = 0$.

According to the underlying principles of the present invention, when the condition $T/L \geq 2$ is not satisfied, then the photovoltage becomes a function of the back surface recombination $S_b$ as expressed by Equation (1). Under constant photon flux conditions, $\phi_{eff}$=constant for all $\alpha$ values used. The photovoltage normalized to the value at a particular wavelength $\lambda$, and thus also a particular absorption coefficient $\alpha$, becomes $$\Delta V^* = \Delta V^{(\alpha)} / \Delta V^{(\alpha_1)}$$

which can be expressed as:

$$\Delta V^*(\alpha) = C_1(T/L) \times \frac{\alpha L^2}{\alpha^2 L^2 - 1} \times \tag{4}$$

$$[(S_b \alpha L - D/L)\sinh(T/L) + (\alpha D - S_b)\cosh(T/L)].$$

This normalized photovoltage depends on $S_b$ but not on $S_f$. Thus, according to the principles of the present invention, the spectral measurements of $\Delta V^*(\alpha)$ can be used for determination of $S_b$ providing that the other wafer parameters in equation (4) are known, such as T and L.

According to a preferred form of the applicant's invention, the sensor for measuring the surface recombination velocity $S_b$ is made of a silicon wafer with a predetermined L value. The ratio T/L is preselected to achieve maximum sensor sensitivity and a suitable range of $S_b$ values, which should correspond to a typical range of surface metal recombination—i.e., from about 1 cm/s to $10^4$ cm/s in silicon.

In determining $S_b$ from equation (4), one can use various methods for fitting an experimental curve $\Delta V^*(\alpha)$ with $S_b$ as a parameter. The method of the present invention is an extension of the basic SPV methods designed for thicker wafers, in that it is also based on determining the effective L value to be denoted $L_m$ for thin wafers. Moreover, it is based further on the observation that even in a range of thin wafers such that a simplifying condition T/L>2 is not satisfied, the plot of $$\frac{1}{\Delta V^*} \text{ vs. } \alpha^{-1}$$

can still be approximated in a reasonable way by a linear dependence $$\frac{1}{\Delta V^*} \simeq \text{const} \times (1 + \alpha^{-1} L_m^{-1}); \tag{5}$$

however the $L_m^{-1}$ value is no longer equal to the minority carrier diffusion length L, but it depends on the T/L ratio and on the $S_b$ value.

The method of the present invention, therefore, proposes to use the $L_m$ value as a sensitive and convenient measure of $S_b$ for wafers where the thickness T is less than the bulk diffusion length $L^\infty$. The method of the present invention can be realized using the types of SPV sensors illustrated in FIGS. 2A, 2B, 3A, 4 and 5. As will be described herein, all these sensors have an exposed back surface which contacts the contaminated fluid in the monitoring system.

SPV measurements are done from the front, illuminated surface using the same procedure and apparatus as in a "linear, constant photon flux" method such as described in applicants' U.S. Pat. No. 5,025,145. The back surface recombination velocity $S_b$ can be determined by fitting $\Delta V^*$ to equation 4, or alternatively using $L_m$ values and computer-stored calibration curves for a given sensor $S_b$ vs. $L_m$ (curves like those shown in FIGS. 6B and 6C). Knowing T and L for the sensor and calibration curve therefore instantaneously yields the $S_b$ value and the corresponding metal contamination.

As indicated above, the concentration of contaminants can be determined from the back surface recombination velocity $S_b$. For low excitation limits (i.e., the low intensity of the light-generating SPV signal), the $S_b$ value is directly proportional to the surface density of the recombination centers, $N_s$:

$$S_b = N_s \cdot v_{th} \cdot \sigma \tag{6}$$

where $v_{th}$ is the thermal velocity of minority carriers (about $10^7$ cm/s in silicon at room temperature) and $\sigma$ is the capture cross sections (typically in the $10^{-15}$ cm$^2$ range). Rough estimation based on the above expression gives $N_s \sim 10^8 \cdot S_b$, and such an $N_s$ is within a surface concentration range ($10^8$/cm$^2$–$10^{12}$/cm$^2$) believed to be significant for silicon microelectronics applications. Thus, since the magnitude of the surface photovoltage $\Delta V$ is dependent on the back surface recombination velocity $S_b$, and $S_b$ is in turn dependent upon the surface density $N_s$ of the recombination centers, and finally since the surface density $N_s$ of the recombination centers is dependent upon the concentration of contaminants in the fluid medium, then the magnitude of the surface photovoltage at the front surface is dependent upon the concentration of contaminants in the fluid medium. Hence, the surface photovoltage $\Delta V$ can be measured at the front surface and used to determine whether undue contamination of the fluid sample has occurred at the back surface.

Figure 6A:
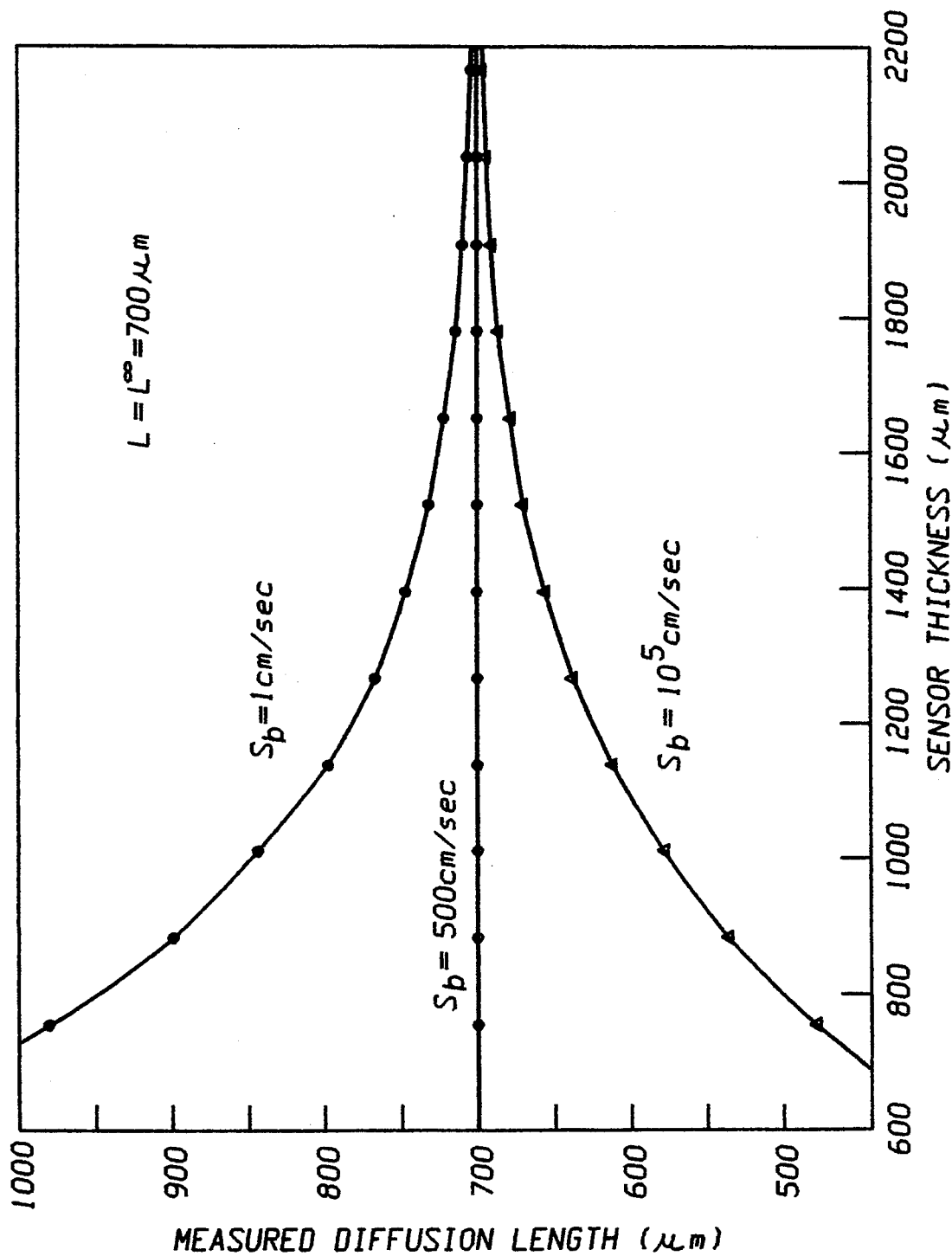
FIG. 6A is a graphical representation of the effect of the sensor thickness on the measured diffusion length value for three different values of surface recombination velocity at the back surface of the sensor wafer.
Figure 6B:
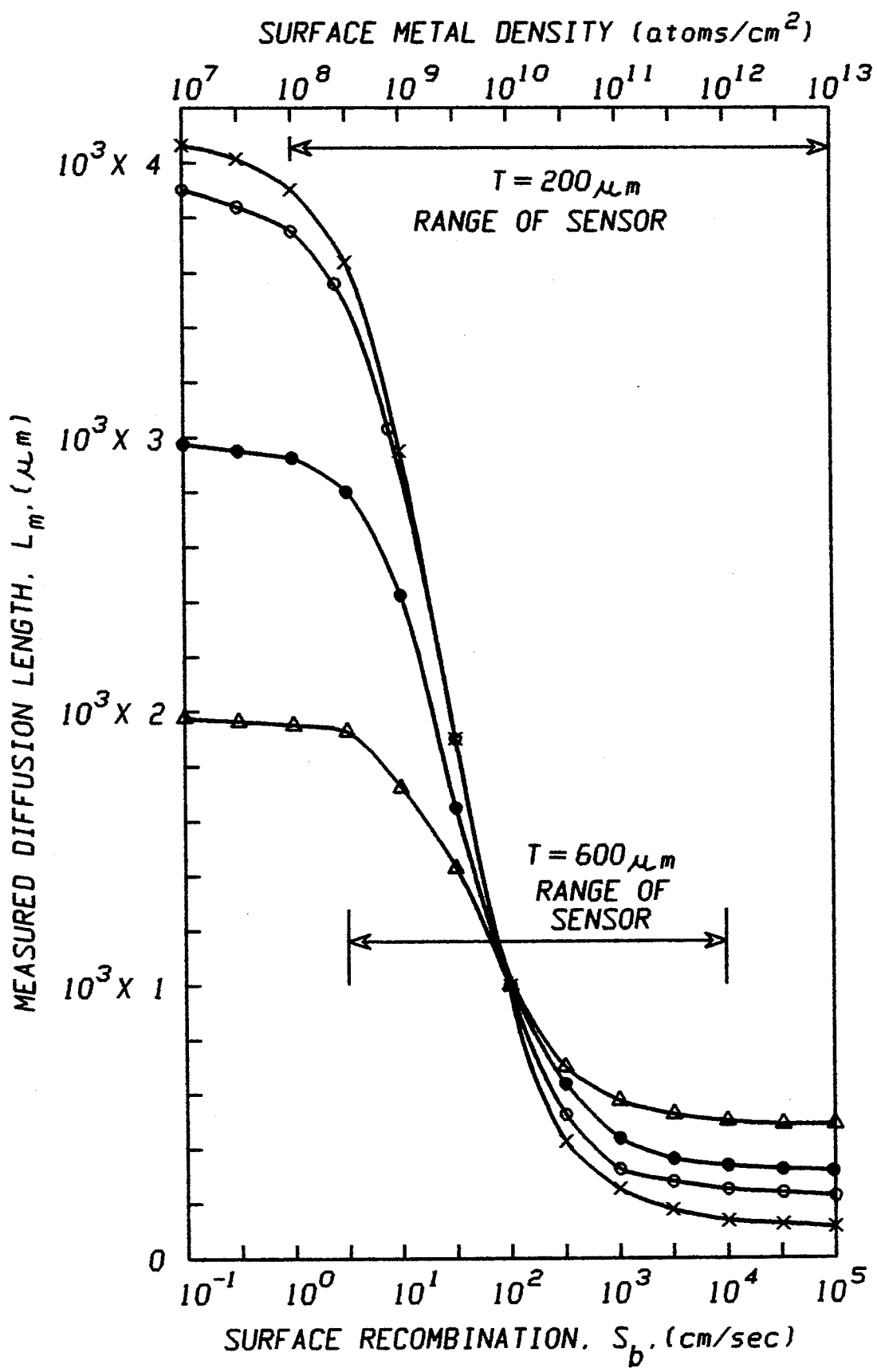
FIG. 6B is a graphical representation of the effect of the back surface recombination velocity and the corresponding surface metal density on the measured diffusion length value for sensors with different thickness.
Figure 6C:
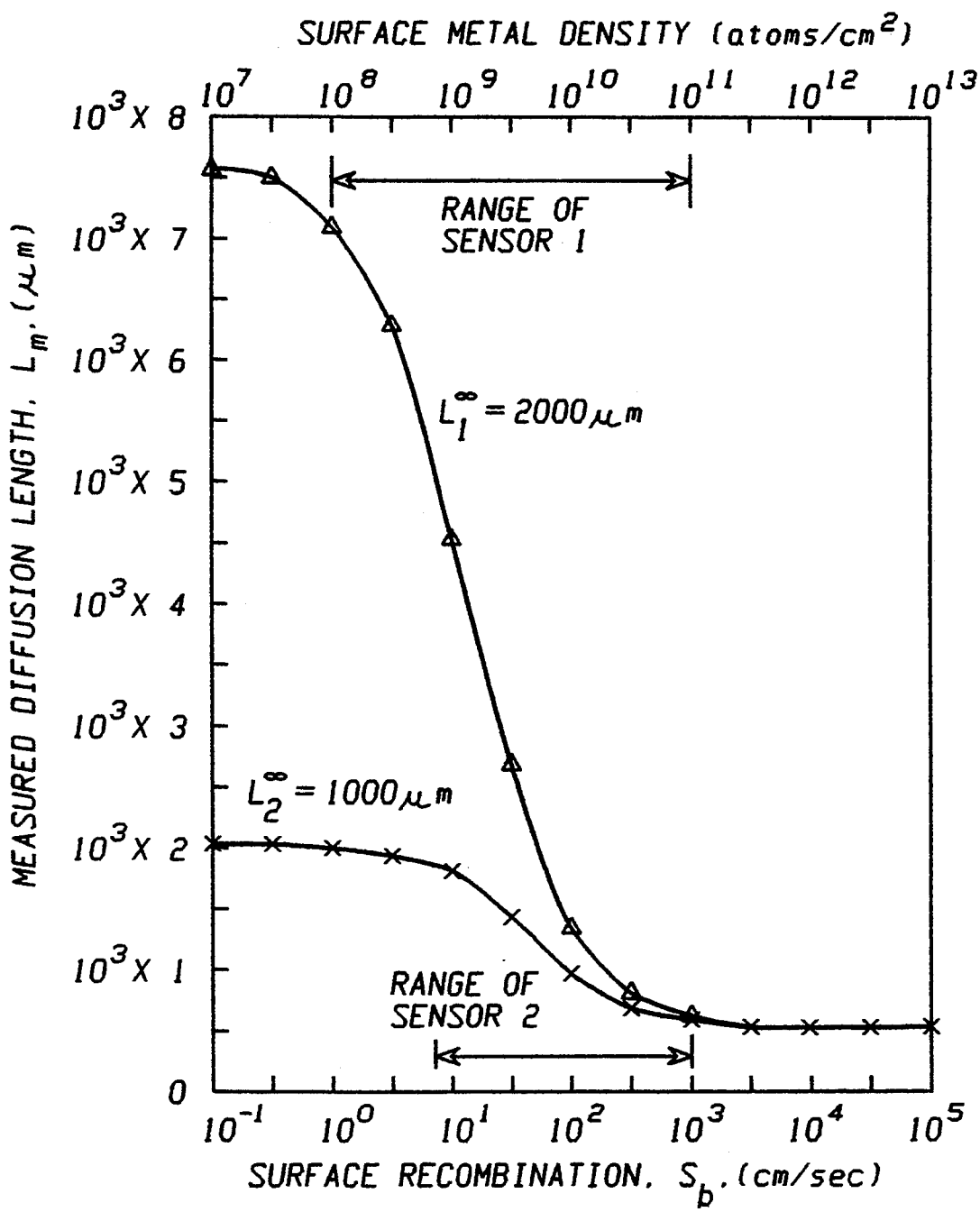
FIG. 6C is a graphical representation of the effect of the back surface recombination velocity and the corresponding surface metal density on the measured diffusion length value for sensors with different diffusion lengths.

FIGS. 6A–6C validate the principle of the thin-wafer sensor configuration discussed above. Most of the plotted values were calculated using highly accurate computer models of the thin-wafer sensor. Additionally, several points were verified by actual measured values.

More particularly, FIG. 6A shows the effect of thinning the sensor, with a bulk diffusion length $L^\infty = 700$ $\mu m$, on the measured diffusion length value, $L_m$, for three different values of surface recombination velocity at the back surface, $S_b$. Note that for low $S_b$ values, $L_m$ increases above the bulk value, and for very high $S_b$ values, $L_m$ decreases below that of $L^\infty$. The difference $\Delta L_m = L_m(\text{low } S_b) - L_m(\text{high } S_b)$ increases with decreasing sensor thickness, thereby increasing the sensor range.

Further, FIG. 6B is a plot of the diffusion length, $L_m$, versus the back surface recombination velocity, $S_b$, and a corresponding surface metal density for sensors with different thickness. For all sensors, $L^\infty = 1,000$ $\mu m$. Note that the sensor range increases with decreasing thickness.

Finally, FIG. 6C is a plot of the diffusion length, $L_m$, versus the back surface recombination velocity, $S_b$, and corresponding surface metal density for 600 $\mu m$ thick sensors with both diffusion length $L_1^\infty = 2,000$ $\mu m$ and $L_2^\infty = 1,000$ $\mu m$. Note that the sensor range increases with increasing $L^\infty$ value.

The measured values in FIGS. 6A–6C were measured using a CMS III device such as disclosed in the applicant's U.S. Pat. No. 5,025,145 on a wafer made of p-type silicon doped with boron to a level of $2 \times 10^{15}$ $cm^{-3}$. The level of surface contamination of copper was known and was applied to the back surface of the wafer from either a buffered HF solution or an $H_2O_2$ solution. It is believed that the actual contaminant used is not important because virtually any metal will provide recombination centers in semiconductor materials. Therefore, the shape of the curves shown in FIGS. 6A–6C are typical of what would be seen if any metal contaminant was used.

Semiconductor Processing System

Figure 2A:
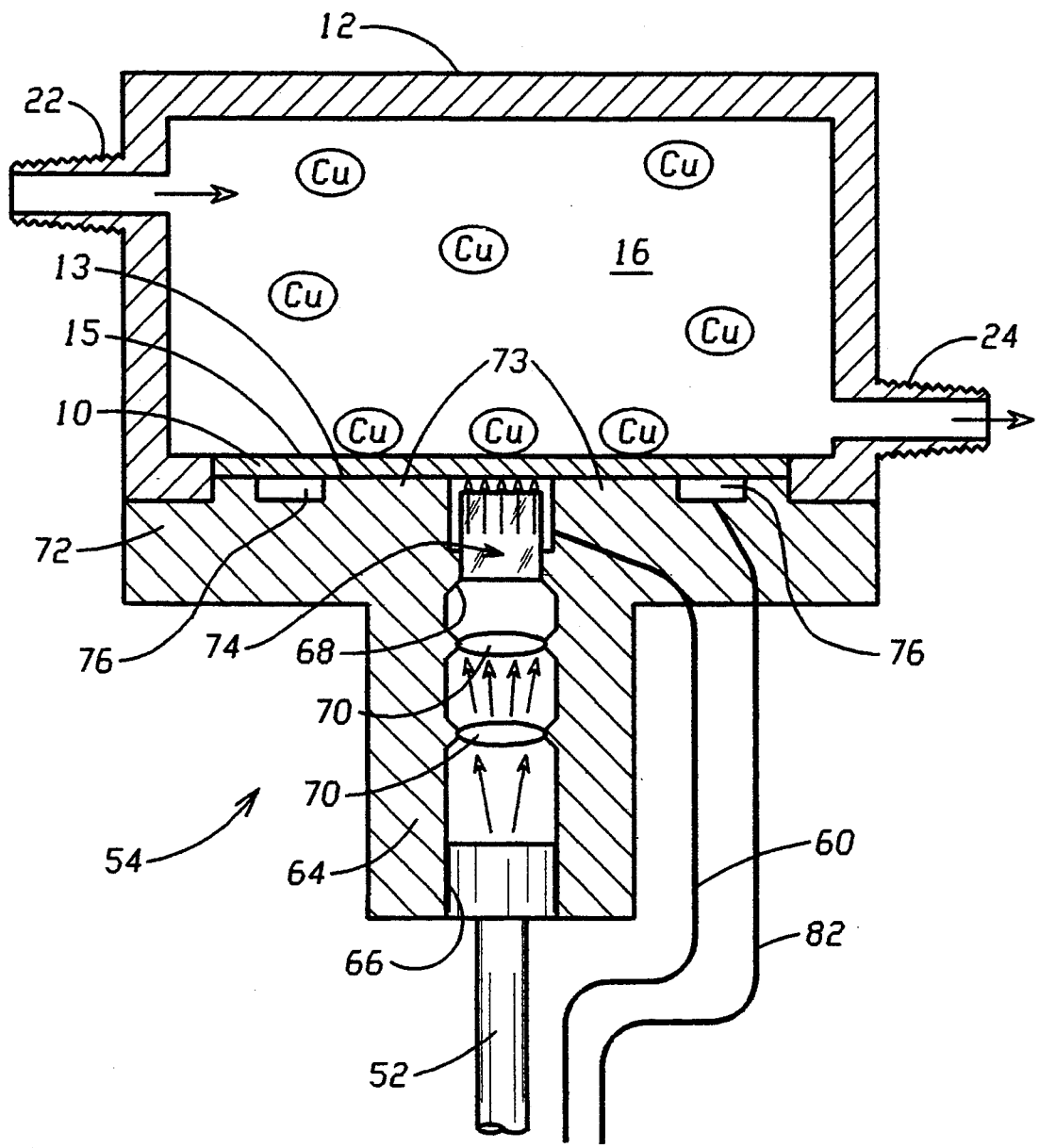
FIGS. 2A and 2B are schematic illustrations of a portion of the semiconductor processing system of FIG. 1 showing one type of sensor and probe constructed according to the present invention.
Figure 2B:
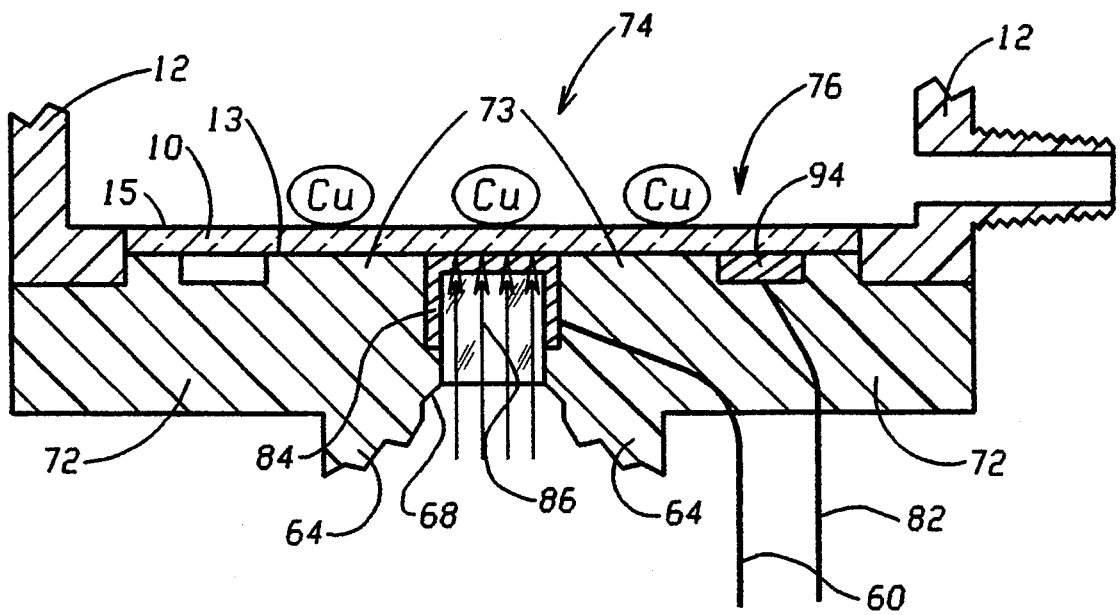

A semiconductor processing system with an SPV sensor constructed according to the invention is schematically illustrated in FIG. 1, while a more detailed illustration of a sensor for the processing system is indicated generally at 10 in FIGS. 2A and 2B. The sensor 10 comprises a p-type silicon wafer, polished and etched on both sides, which is mounted by e.g., teflon O-rings, to the bottom of a teflon fluid testing chamber 12. The silicon used for the sensor must be of very high purity, with a bulk diffusion length of about 1,000 $\mu m$ or higher and a thickness of about 400 $\mu m$.

Surface preparation of the sensor wafer should satisfy two conditions: (1) a depletion type surface barrier on the front surface 13 (e.g., a P-N junction or any other rectifying contact suitable for generation of a photovoltage); and (2) a very low surface recombination on the back surface 15 facing and in direct contact with fluid 16 in the testing chamber 12. The low original surface recombination value on the back surface 15 is necessary to enhance the detection sensitivity for contaminants deposited from the liquid.

The fluid testing chamber 12 of the semiconductor processing system includes a fluid inlet 22 and a fluid outlet 24. The fluid inlet 22 is connected to a fluid reservoir 26. The fluid outlet 24 is connected to a fluid pump 27. A semiconductor wafer processing station 28 is connected between the fluid pump 27 and the fluid reservoir 26 for re-use. The fluid pump 27 directs the fluid into the wafer processing station 28, and fluid from the processing station 28 is directed back to the fluid reservoir 26. Alternatively, the fluid from the wafer processing station 28 can be connected to a discharge reservoir (not shown) and not be re-used. In any case, in the processing system of FIG. 1, the fluid testing chamber 12 is "in line" with, and upstream of, the wafer processing station 28.

Nevertheless, it should be apparent to those skilled in the art that the above-described processing system is only exemplary in nature, and other types of processing systems can also be used with the sensor of the present invention. In other words, the sensor of the present invention has wide adaptability to many types of commercially-used processing systems for manufacturing integrated circuits.

The sensor 10 forms part of the fluid testing chamber 12 and is attached thereto (e.g., sealed around the edges) in any conventional manner. The back surface 15 of the sensor 10 is in contact with the fluid in the testing chamber 12 as the fluid passes on the way to the wafer processing station 28. A photovoltaic generating/measuring device, indicated generally at 32, is associated with the front surface 13 of the sensor 10, as will be described more fully hereinafter.

As discussed in applicant's U.S. Pat. No. 5,025,145, the generator/measuring device 32 preferably employs a quartz halogen bulb 34 held in a source housing 36. Radiation produced by the bulb is focused and passed first through a rotating chopper 38 held within the source housing 36. The rotating chopper is operated at a selected frequency in the range between 5 Hz–100 Hz for direct contact SPV measurements, and between 500 Hz–600 Hz for capacitive-coupled SPV measurements. Following the chopper 38 is the light intensity attenuator 39, an iris diaphragm 40 and a graduated variable neutral density filter 42, held in an assembly housing 44. The attenuator 39 is adjustable for increasing or decreasing light intensity in the linearity measurement procedure to be described below.

After passing through the filters, the attenuated beam is focused onto a first glass fiber optical cable 46 which is coupled by e.g., adhesive epoxy, to the filter assembly 48 by means of, e.g., cable mounts. The optical cable 46 brings radiation from the bulb 34, modulated by the chopper 38 to a filter wheel 50 which may be used for wavelength selection. Each filter in the filter wheel 50 consists of a narrow band pass filter and a customized set of neutral density filters, the former assuring substantially monochromatic light and the latter being used to achieve a substantially constant photon flux $\phi_{eff.} = \text{const}$.

After passing through a selected filter of the filter wheel 50, the monochromatic beam is coupled to a fiber optical cable 52 which directs the radiation toward the front surface 13 of the sensor 10 (see FIG. 2). The use of the fiber optical cables in this preferred embodiment provides a particular advantage of the apparatus in that the system need not be entirely shaded from ambient light which might otherwise cause measurement errors or increased noise in conventional open optic designs.

The light incident upon the sensor 10 generates a photovoltage which is detected by a probe, indicated generally at 54, which is connected to a lock-in amplifier 56 of an electronic system via a lead 60. The probe 54 is also electrically connected to the lock-in amplifier 56 via reference ground lead 82. The electronic system further includes a control along lead 58 for the light source chopper 38 which provides a reference signal for the lock-in amplifier 56.

The filter wheel 50 includes eight filters (labeled 1-8 in FIG. 1) which may be selectively positioned in the radiation path of the optical cable 52 by rotating filter wheel 50. Two filters for use in the linearity check, for example, filters 1 and 2, transmit white light and have an intensity ratio of $I_1/I_2 = 2.00 \pm 0.05$. Filters 3-8 are composed of the narrow band (half width, e.g., $\leq 0.01$ ev) pass interference filters that transmit monochromatic radiation and the customized neutral density filters which assure a similar photon flux within $\pm 2\%$ for use in minority carrier diffusion length measurements. An example of a set of filter characteristics for the measurement of diffusion length L in silicon wafers are given in Table I below:

| Wheel Position | Photon Energy (in eV) | Output Effective Photon Flux (arb. units) |
|---|---|---|
| 3 | 1.210 | 1.00 |
| 4 | 1.240 | 0.98 |
| 5 | 1.269 | 1.02 |
| 6 | 1.303 | 1.00 |
| 7 | 1.340 | 0.99 |
| 8 | 1.380 | 1.01 |

The probe 54 accepts the optical cable 52 and directs the radiation to the sensor front surface 13 and detects the induced photovoltage. The probe 54 may be supported on a vertical positioner which allows raising and lowering the probe relative to the front surface 13 of the sensor 10.

The probe 54 includes a jacket 64 constructed from a material such as a dark plastic which is not transparent to light and comprises a first aperture 66 for receiving the fiber optic cable 52 which may be attached sealably or via common couplers, and a second aperture 68 disposed opposite the first aperture for vertical direction of the provided radiation. The second aperture 68 defines the photovoltage probing area on the wafer which is approximately equal to the cross-sectional area of the second aperture. Preferably, between the first and second apertures and beyond the point at which the fiber optic cable terminates in the probe jacket 64, one or more lens 70 are provided for forming a uniform beam of radiation through the second aperture 68. About the second aperture 68, the jacket 64 forms a base region 72 which is of substantially greater outside diameter than the aperture 68, for example, the outer diameter of the base region 72 is preferably about 25 mm, while the diameter of the aperture 68 is about 2 mm.

The probe 54 is provided with a semi-transparent pickup electrode assembly 74 and a reference ground assembly 76, which will be explained in further detail below. The electrode assembly, shown generally at 74, and the reference ground assembly shown generally at 76 are anchored to the base region 72 of the jacket 64. The electrode assembly 74 will typically comprise a roughly circular area. The reference ground assembly 76 may comprise a single, roughly circular area or an annular ring or rectangular shape around the electrode assembly 74.

The base region 72 has a light shield 76, which is substantially flush against the front surface 13 of the sensor 10. The light shield 76 surrounds the electrode assembly 74 and may be annular ring-shaped or rectangular in shape, for example.

According to one embodiment of the present invention, shown in FIG. 2B, the electrode assembly 74 includes a semi-transparent flexible foil photovoltage pickup electrode 84, made of, for example, indium-tin oxide, covering a semi-transparent block 86, made of, for example, quartz. The electrode assembly has associated with it an electrode lead 60, which connects directly to the lock-in amplifier 56.

The reference ground assembly includes a reference ground electrode 94, which can also be made of e.g., indium-tin oxide, and has associated with it a reference ground lead 82, which electrically communicates the reference signal from the lock-in amplifier 56.

Light from the fiber optic cable 52 passes through lens 70, the semi-transparent block 86, and the semi-transparent flexible foil photovoltage pickup electrode 84. The light impinges upon the front surface 13 of the sensor 10 and creates a photovoltaic effect dependent upon the concentration of contaminants in contact with the back surface 15 of the sensor. For example, the light can create a surface photovoltage at the front surface in the absence of any junctions on the wafer; or can create a photovoltage near the surface of the wafer if other photovoltaic techniques are used, e.g., P-N junction photovoltage or semi-conductor photovoltage.

In any case, the electrode pickup 74 senses the photovoltage and relays this information to lock-in amplifier 56, which then provides an output signal to computer 79 which digitizes the signal and provides an indication of the contaminants in the fluid.

The computer 79 then uses a series of $\Delta V$ measurements to calculate the minority carrier diffusion length, $L_m$. $L_m$ is used to calculate the back surface recombination velocity, $S_b$, which is, in turn, used to calculate the surface concentration of contaminants, $N_s$.

The light shield 73 of the base 72 performs two functions. First, stray background light is blocked from the surface area interrogated because the light shield 73 is i) flush against the front surface 13 of the wafer 10, ii) surrounds the electrode assembly 74, and iii) the front surface 13 of the wafer is larger than the wafer area imaged by the beam and measured by the pickup electrode. This design represents a significant improvement over previous surface photovoltage probes by permitting the use of the probe in the presence of ambient light and thereby avoiding the inconvenience of shading the entire wafer, while still reducing noise levels in the measurement.

Figure 3A:
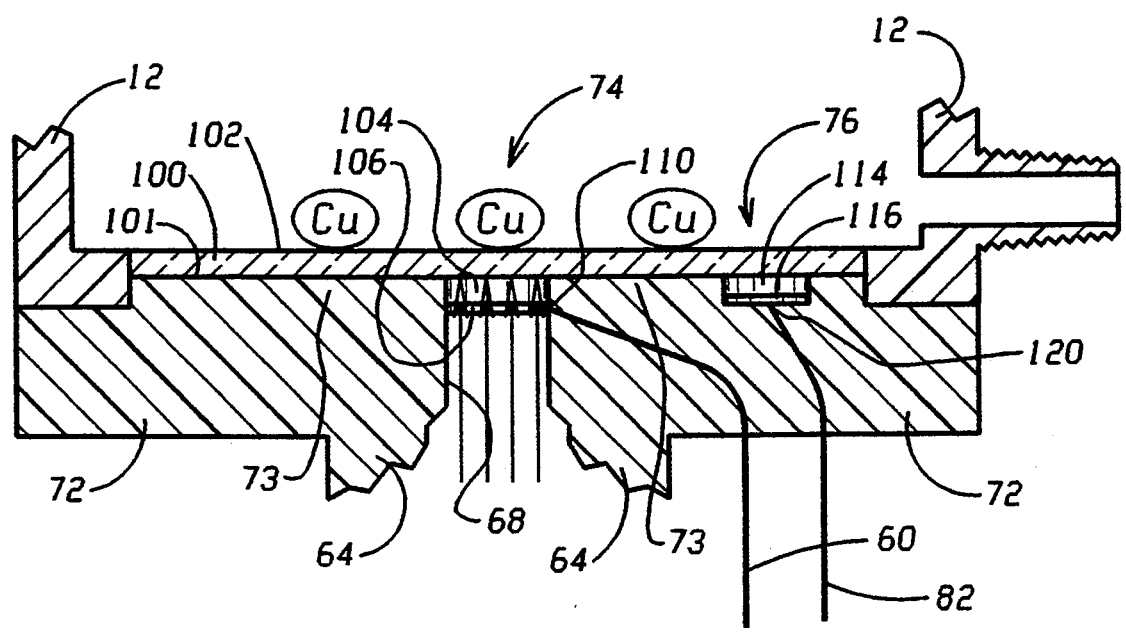
FIG. 3A is a schematic illustration of another type of sensor and probe structure for the present invention.

Referring now to FIG. 3A, a preferred embodiment of the probe 54 and the sensor 10 is illustrated. In FIG. 3A, a MOS-type sensor 100 is shown formed from p-type silicon. In the MOS-type sensor 100, the electrode assembly 54 and the reference ground assembly 76 of the probe 74 capacitively couple the SPV. The sensor 100 has a front surface 101 and a back surface 102. The electrode assembly 74 of the probe 54 includes a transparent dielectric 104 deposited on the front surface 101 of the sensor 100. The semi-transparent dielectric 104 may be a typical dielectric such as $SiO_2$ or $Si_3N_4$, and may be grown or deposited directly onto the front surface 101 of the sensor 100.

A semi-transparent pickup electrode 106 is deposited on the outer surface of the semi-transparent dielectric 104. The semi-transparent pickup electrode 106 may be made of semi-transparent metal (about 200 Å thick) evaporated onto the semi-transparent dielectric 104. The semi-transparent pickup electrode 106 should be smaller than the front surface 101 of the sensor 102, and should be transparent enough to allow light from the second aperture 68 of probe 54 to pass through to the front surface 101, allowing the light to generate electron hole pairs, and therefore, a surface photovoltage.

The semi-transparent pickup electrode 106 has signal lead 60 connected at a pickup contact 110. The pickup lead 60 connects to a high input resistance preamplifier and the lock-in amplifier 56 (FIG. 1).

In this preferred embodiment, the reference ground assembly 76 of the probe 54 is also attached to the front surface 101 of the sensor 100. The reference ground electrode 116 may be a metal deposited directly on silicon or on the dielectric film.

The reference ground electrode 116 has associated with it a reference ground lead 82 which is communicated with a preamplifier and the lock-in amplifier.

Figure 3B:
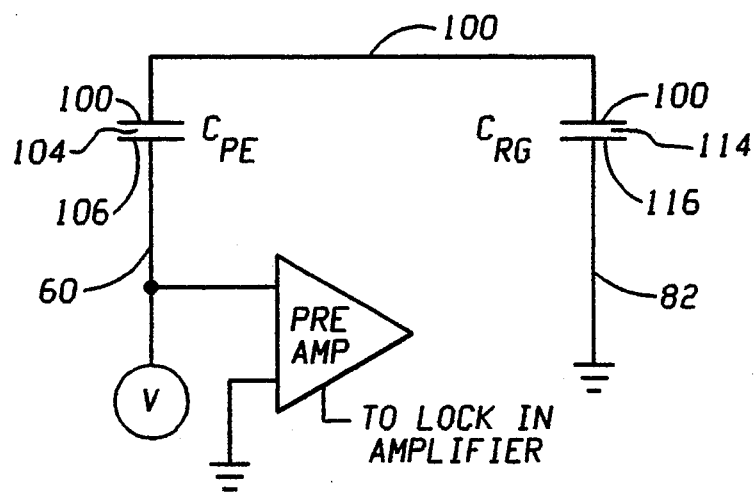
FIG. 3B is an electrical schematic drawing of the capacitive coupling of the sensor and probe structure of FIG. 3A.

Referring now to FIG. 3B, an electrical schematic view of the capacitive coupling of the MOS-type sensor 100 of FIG. 3A is shown. The sensor 100 and the semi-transparent pickup electrode 106 form a capacitor $C_{PE}$ 130 with the semi-transparent dielectric 104 acting as the dielectric medium. Also, the sensor 100 and the reference ground electrode 116 form a capacitor $C_{RG}$ 132. The reference ground lead 82 and the pickup lead 60 and the input resistor of the preamplifier complete the circuit shown in FIG. 3B.

Additional modifications and variations of the present invention are possible.

Figure 4:
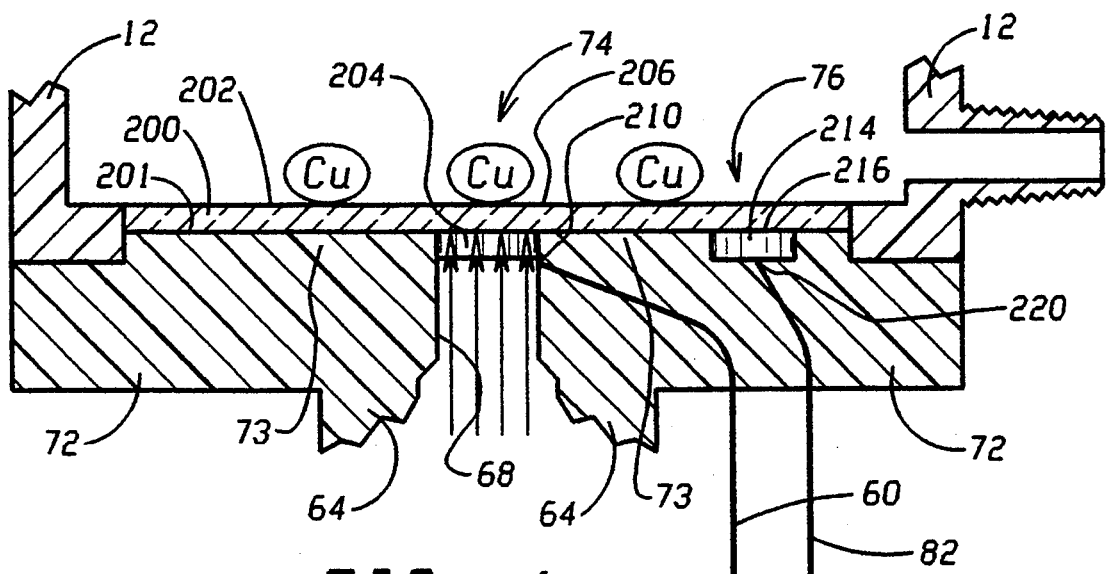
FIG. 4 is a schematic illustration of a third type of sensor and probe structure for the present invention.

For example, referring now to FIG. 4, a further embodiment of a sensor is shown with a P-N type junction. According to this embodiment, a sensor 200 is formed of p-type silicon. The sensor 200 has a front surface 201 and a back surface 202. The electrode assembly 74 of the probe 54 includes a pickup N+ region 204 grown directly onto or doped into the front surface 201 of the sensor 200, which is sufficiently thin to be transparent to an SPV generating light beam. The pickup N+ region 204 forms a P-N junction on which the photovoltage is generated. The pickup N+ region 204 has a signal pickup lead 60 associated with it which connects to the pickup N+ region 204 at a pickup contact 210. The pickup lead 60 connects directly to the preamplifier and the lock-in amplifier 56 (FIG. 1). Again, as described previously, the pickup N+ region 204 should be smaller than the front surface 201 of the sensor 200 and must allow light from the second aperture 68 of the probe 54 to pass through to the sensor 200 below, allowing the light to generate electron whole pairs and therefore a photovoltage.

The reference ground assembly 76 for this embodiment has a reference ground ohmic contact (evaporated AL) to p-type base region at the sensor.

Again, as described with respect to the previous embodiment, the P-N junction-type sensor 200 has a thickness T which is less than the bulk diffusion length, $L^\infty$. Further, the back surface 202 of the sensor 200 is in direct contact with the fluid 16 being measured by the sensor.

Figure 5:
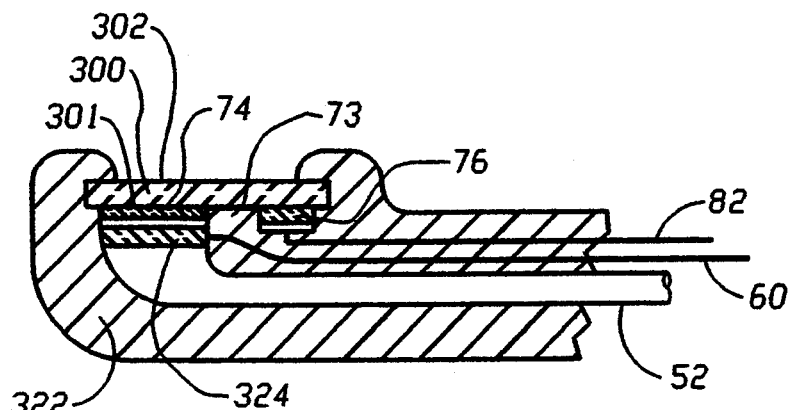
FIG. 5 is a schematic illustration of an additional aspect of the present invention wherein a portion of the sensor and probe are encapsulated.

Referring now to FIG. 5, an encapsulated miniature sensor 300 is shown made according to another embodiment of the present invention. This sensor could be manufactured in an integrated miniaturized form and is suitable for emersion into the liquid being monitored. The encapsulated miniature sensor could be made like any of the types of systems previously described, such as the MOS-type sensor 100, the P-N junction-type sensor 200, or the flexible foil electrode sensor 10. The encapsulated miniature sensor 300 has a front surface 301 which is illuminated and a back surface 302 which is exposed to the fluid 16 being monitored.

The sensor 300 with the associated pickup electrode assembly 304 and the reference ground assembly 314 is encapsulated in an encapsulation medium 322, which covers most of the encapsulated miniature sensor 300, except for a portion of the back surface 301 corresponding to the illuminated portion of the front surface 301. The exposed portion of the back surface 301 is in contact with the fluid being monitored. The encapsulation medium 322 should be formed from a material which is resistant to damage which may be caused by the harsh fluids used in semiconductor processing (e.g., teflon). Moreover, in this embodiment, a portion of the encapsulation medium 322 can form the light shield 73.

The examples shown in this specification refer to systems having sensors made of p-type silicon and several regions are denoted as N+ regions. P-type silicon sensors are preferred because the bulk minority carrier diffusion length $L^\infty$ in p-type silicon is longer than that in n-type silicon. However, for some applications, an n-type sensor may also be suitable.

Other modifications of the present invention are also possible when considered in light of the above teachings. It is therefore understood that the scope of the present invention is not to be limited to the details disclosed herein, and may be practiced otherwise than as specifically described, and is intended only to be limited by the claims appended hereto.

What is claimed is:

1. A system for measuring contamination of a fluid medium, comprising:
   (a) a sensor having a back surface and a front surface, said back surface being in direct contact with a sample of the fluid medium, said sensor being made of material which is reactive with semiconductor contaminants to form recombination centers at said back surface and to enable diffusion of electrons and holes therethrough, said sensor having a bulk diffusion length and a thickness such that the magnitude of a photovoltaic effect developed at or near said front surface by means of light at a predetermined excitation state is dependent on the concentration of recombination centers on the back surface; and
   (b) photovoltaic generating and measuring means for (i) directing light at said predetermined excitation state at said front surface to develop the photovoltaic effect at or near said front surface and (ii) measuring the magnitude of the photovoltaic effect at or near said front surface.

2. A system as defined in claim 1 wherein the thickness of said sensor is no greater than its bulk diffusion length.

3. A system as defined in claim 2 wherein said sensor is formed of substantially pure silicon.

4. A system as defined in claim 3 wherein said sensor has the configuration of a thin wafer, said back surface has a surface configuration which has a very low surface recombination value and said front surface has a depletion type surface barrier for generating the photovoltaic effect.

5. A system as defined in claim 4, wherein said front surface has a configuration which generates a surface photovoltage.

6. A system as defined in any of claims 1–5, further including a semiconductor processing chamber and a sensing chamber disposed upstream of said semiconductor processing chamber, said sensing chamber having an inlet for receiving a sample of said fluid medium and an outlet for directing said sample of said fluid medium into said semiconductor processing chamber, said sensor forming at least part of said sensing chamber with said back surface of said sensor disposed for direct contact with a fluid medium located in said sensing chamber.

7. A system as defined in claim 1 wherein said photovoltaic generating and measuring means comprises;
   (a) a light source for producing a light signal,
   (b) means for controlling the intensity of said light signal,
   (c) means for controlling the wave form of said light signal,
   (d) means for controlling the wavelength of said light signal;
   (e) a probe for sensing the photovoltaic effect developed at or near said front surface; and
   (f) a detection circuit for measuring the magnitude of the photovoltaic effect sensed by said probe.

8. A system as defined in claims 1 or 7, wherein said probe includes:
   (i) an electrode assembly having an associated electrode lead, said electrode lead being electrically connected to said photovoltaic generating and measuring means, and said electrode assembly couples surface photovoltage from said front surface to said electrode lead; and
   (ii) a reference ground assembly having an associated reference ground lead, said reference ground lead being electrically connected to said photovoltaic generating and measuring means.

9. A system as defined in claim 8 wherein said electrode assembly comprises a semi-transparent dielectric attached to said front surface of said sensor, and a semi-transparent pickup electrode substantially the same size as said semi-transparent dielectric and attached to said semi-transparent dielectric at the side opposite the side attached to said front surface; and
   wherein said reference ground assembly comprises a reference ground dielectric attached to said front surface of said sensor, and a reference ground electrode substantially the same size as said reference ground dielectric and attached to said reference ground dielectric at the side opposite the side attached to said front surface.

10. A system as defined in claim 9, wherein said semi-transparent dielectric and said reference ground dielectric comprise $SiO_2$ or $Si_3N_4$ material grown onto said front surface.

11. A system as defined in claim 9 wherein said semi-transparent pickup electrode and said reference ground electrode comprise a thin coating of metal deposited onto said semi-transparent dielectric and said reference ground dielectric.

12. A system as defined in claim 11, wherein said thin coating of metal on said semi-transparent dielectric and said reference ground dielectric and said reference ground dielectric is about 200 Å thick.

13. A system as defined in claim 8 wherein said electrode assembly comprises an N+ region formed at the front surface of said sensor.

14. A system as defined in claim 8 wherein said electrode assembly comprises an indium tin oxide electrode.

15. A system as defined in claim 8 further including:
   (i) an optical cable for transmitting light at said predetermined excitation state from said photovoltaic generating and measuring means through said electrode assembly to said front surface;
   (ii) an optical coupler, wherein said optical coupler optically connects said optical cable to said electrode assembly; and
   (iii) an encapsulation medium, said encapsulation medium at least partially encapsulating said front surface, said optical coupler, said electrode assembly, and said reference ground assembly.

16. A system as defined in claim 15, wherein said probe includes a light shield supported proximate said front surface of said sensor and surrounding said electrode assembly to shield the front surface from ambient light.

17. A method for producing integrated circuitry in a semiconductor material, comprising the steps of:
   (a) providing a fluid medium for use in semiconductor processing during production of integrated circuitry in a semiconductor material;
   (b) providing a sensor comprising a mass of sensing material having front and back surfaces, said mass of material being reactive with semiconductor contaminants in the fluid medium to form recombination centers at said back surface and to enable diffusion of electrons and holes therethrough, said sensor having a bulk diffusion length and a thickness which causes the magnitude of a photovoltaic effect developed at or near said front surface by means of light at a predetermined excitation state to be dependent on the concentration of semiconductor contaminants in the fluid medium,
   (c) flowing a sample of the fluid medium into direct contact with said back surface of said mass of sensing material,
   (d) developing the photovoltaic effect at or near said front surface by means of light in said predetermined excitation state and measuring the magnitude of the photovoltaic effect developed at or near said front surface of said mass of sensing material to determine if the sample of the fluid medium has a predetermined concentration of semiconductor contaminants, and
   (e) if the sample of the fluid medium has less than the predetermined concentration of semiconductor contaminants, using the fluid medium to flow into contact with the semiconductor material as part of the production of an integrated circuit in the semiconductor material.

18. A sensor structure for use in determining if a sample of a fluid medium has semiconductor contaminants therein, said sensor structure comprising:
   (a) a substantially flat wafer formed of semiconductor material;
   (b) said wafer having front and back surfaces;
   (c) said wafer being reactive with semiconductor contaminants in direct contact with its back surface to form recombination centers at said back surface; and
   (d) said wafer having a bulk diffusion length and a thickness such that a photovoltaic effect developed at or near said front surface by means of light in a predetermined excitation state is dependent upon the density of recombination centers which form at said back surface of said wafer due to semiconductor contaminants in the sample of the fluid medium.

19. A sensor structure as defined in claim 18 wherein the thickness of said wafer is no greater than its bulk diffusion length.

20. A sensor structure as defined in claim 19 wherein said wafer is formed of substantially pure silicon.

21. A sensor structure as defined in claim 20 wherein said back surface of said wafer has a surface configuration which has a very low surface recombination value and said front surface has a depletion type surface barrier.

22. A sensor structure as defined in claim 18 wherein said sensor structure further includes;
   (a) a light source for producing a light signal,
   (b) means for controlling the intensity of said light signal,
   (c) means for controlling the wave form of said light signal,
   (d) means for controlling the wavelength of said light signal;
   (e) a probe for sensing the photovoltaic effect developed at or near said front surface of the wafer; and
   (f) a detection circuit for measuring the magnitude of the photovoltaic effect sensed by said probe.

23. A sensor structure as defined in claim 22, wherein said probe includes:
   (i) an electrode assembly having an associated electrode lead, said electrode lead being electrically connected to said sensor structure, and said electrode assembly couples surface photovoltage from said front surface to said electrode lead; and
   (ii) a reference ground assembly having an associated reference ground lead, said reference ground lead being electrically connected to said sensor structure.

24. A sensor structure as defined in claim 23 wherein said electrode assembly comprises a semi-transparent dielectric attached to said front surface of said wafer, and a semi-transparent pickup electrode substantially the same size as said semi-transparent dielectric and attached to said semi-transparent dielectric at the side opposite the side attached to said front surface; and
   wherein said reference ground assembly comprises a reference ground dielectric attached to said front surface of said wafer, and a reference ground electrode substantially the same size as said reference ground dielectric and attached to said reference ground dielectric at the side opposite the side attached to said front surface.

25. A sensor structure as defined in claim 24, wherein said semi-transparent dielectric and said reference ground dielectric comprise $SiO_2$ or $Si_3N_4$ material grown onto said front surface.

26. A sensor structure as defined in claim 24 wherein said semi-transparent pickup electrode and said reference ground electrode comprise a thin coating of metal deposited onto said semi-transparent dielectric and said reference ground dielectric.

27. A sensor structure as defined in claim 26, wherein said thin coating of metal on said semi-transparent dielectric and said reference ground dielectric is about 200 Å thick.

28. A sensor structure as defined in claim 23 wherein said electrode assembly comprises an N+ region formed at the front surface of said wafer.

29. A sensor structure as defined in claim 23 wherein said electrode assembly comprises an indium tin oxide electrode.

30. A sensor structure as defined in claim 23 further including:
   (i) an optical cable for transmitting light at said predetermined excitation state from said sensor structure through said electrode assembly to said front surface;
   (ii) an optical coupler, wherein said optical coupler optically connects said optical cable to said electrode assembly; and
   (iii) an encapsulation medium, said encapsulation medium at least partially encapsulating said front surface, said optical coupler, said electrode assembly, and said reference ground assembly.

31. A sensor structure as defined in claim 30, wherein said probe includes a light shield supported proximate said front surface of said wafer and surrounding said electrode assembly to shield the front surface from ambient light.

32. A sensor structure for use in determining if a sample of a fluid medium has semiconductor contaminants therein, said sensor structure comprising:
   (a) a substantially flat wafer formed of semiconductor material;
   (b) said wafer having front and back surfaces;
   (c) said wafer being reactive with semiconductor contaminants in direct contact with its back surface to form recombination centers at said back surface;
   (d) said wafer having a bulk diffusion length and a thickness such that a photovoltaic effect developed at or near said front surface by means of light in a predetermined excitation state is dependent upon the density of recombination centers which form at said back surface of said wafer due to semiconductor contaminants in the sample of the fluid medium; and
   (e) wherein said back surface of said wafer has a surface configuration which has a very low surface recombination value and said front surface has a depletion type surface barrier.

33. A sensor structure for use in determining if a sample of a fluid medium has semiconductor contaminants therein, said sensor structure comprising:
   (a) a substantially flat wafer formed of semiconductor material, said wafer having front and back surfaces;
   (b) a semi-transparent dielectric attached to said front surface of said wafer, and a semi-transparent pickup electrode substantially the same size as said semi-transparent dielectric and attached to said semi-transparent dielectric at the side opposite the side attached to said front surface;
   (c) a reference ground dielectric attached to said front surface of said wafer, and a reference ground electrode substantially the same size as said reference ground dielectric and attached to said reference ground dielectric at the side opposite the side attached to said front surface;
   (d) said wafer being reactive with semiconductor contaminants in direct contact with its back surface to form recombination centers at said back surface; and
   (e) said wafer having a bulk diffusion length and a thickness such that a photovoltaic effect developed at or near said front surface by means of light in a predetermined excitation state is dependent upon the density of recombination centers which form at said back surface of said wafer due to semiconductor contaminants in the sample of the fluid medium.

* * * * *